United States Patent
Abdel-Rahman et al.

[11] Patent Number: 5,889,404
[45] Date of Patent: Mar. 30, 1999

[54] DISCHARGE IONIZATION DETECTOR HAVING EFFICIENT TRANSFER OF METASTABLES FOR IONIZATION OF SAMPLE MOLECULES

[75] Inventors: Mahmoud F. Abdel-Rahman, West Grove, Pa.; William H. Wilson, Newark, Del.

[73] Assignee: Hewlett-Packard Company, Palo Alto, Calif.

[21] Appl. No.: 921,412

[22] Filed: Aug. 29, 1997

[51] Int. Cl.[6] .................................................. G01N 27/62
[52] U.S. Cl. .......................... 324/464; 324/71.1; 324/465; 73/28.02; 250/423 R
[58] Field of Search ..................... 324/459, 464, 324/465, 468, 470, 71.1, 71.4, 123 R; 73/28.02, 28.04; 313/231.41, 231.71; 315/111.01, 111.08, 111.09, 362.1; 250/374, 382, 385.1, 385.2, 389, 423 R, 423 F, 426, 427; 436/153

[56] References Cited

U.S. PATENT DOCUMENTS

| | | | |
|---|---|---|---|
| 4,220,545 | 9/1980 | Franzen et al. | 250/423 R |
| 4,304,997 | 12/1981 | Sullivan et al. | 324/465 |
| 4,739,214 | 4/1988 | Barr | 250/423 R |
| 4,789,783 | 12/1988 | Cook | 250/379 |
| 4,934,456 | 6/1990 | Grim et al. | 250/423 R |
| 4,975,648 | 12/1990 | Lawson et al. | 324/464 |
| 5,153,519 | 10/1992 | Wentworth et al. | 324/464 |
| 5,192,865 | 3/1993 | Zhu | 250/288 |

OTHER PUBLICATIONS

G. Gremaud, W.E. Wentworth, A. Zlatkis, R. Swatloski, E.C.M. Chen, S. Stearns, "Windowless Pulsed–Discharge Photoionization Detector Application To Qualitative Analysis Of Volatile Organic Compounds", accepted Aug. 18, 1995, Journal of Chromatography A. 724 (1996) pp. 235–250.

*Primary Examiner*—Diep N. Do
*Attorney, Agent, or Firm*—Mark Z. Dudley

[57] ABSTRACT

In a discharge ionization detector, a method and apparatus are disclosed for increasing the transfer of photons and metastables from a discharge chamber to a ionization chamber, while effecting ion discrimination of the ionic current with respect to a signal cathode, thereby reducing the effect of ionic current in the signal output. Preferred embodiments of the invention include a discharge source located in a discharge chamber, means for introducing discharge gas flow into the discharge chamber, a flow guide that directs discharge gas flow between the discharge chamber and an adjacent ionization chamber, and inlet port for introducing a flow of sample gas containing an analyte into the ionization chamber and an outlet port for exhausting the sample gas and the discharge gas. A plurality of apertures in the flow guide are situated proximate the discharge source so as to promote the rapid and efficient transfer of photons and metastables from the discharge source into the ionization chamber. A signal cathode and the ionization chamber are biased in a circuit with an electrometer so as to provide a detector output signal.

10 Claims, 5 Drawing Sheets

DISCHARGE IONIZATION DETECTOR HAVING EFFICIENT TRANSFER OF METASTABLES FOR IONIZATION OF SAMPLE MOLECULES

FIELD OF THE INVENTION

This invention relates generally to detectors for analysis of a sample gas; and more particularly, to discharge ionization detectors.

BACKGROUND OF THE INVENTION

A discharge ionization detector operates by applying a high voltage across discharge electrodes that are located in a gas-filled discharge chamber. In the presence of helium, a characteristic discharge emission of photons occurs. The photons irradiate a port connecting the discharge chamber to an ionization chamber receiving a sample gas that contains an unknown component. Electrons are produced in the ionization chamber as a result of photon interaction with ionizable molecules in the column effluent. Helium metastables are also generated in the discharge chamber and are found to play a role in ionization of the analyte of interest. The magnitude of the ionized analytes is manifested as a current that can be measured to ascertain the composition of one or more components in the analyte.

Discharge ionization detectors are disclosed in U.S. Pat. Nos. 4,789,783; 4,975,648; and 5,153,519. As disclosed in U.S. Pat. No. 4,975,648, the geometry of the two chambers and of the emitter/collector electrodes in the detector are said to be important to the efficient operation of the detector, and the collector and emitter electrodes are said to be shaped and positioned relative to the inlet for the sample gas and to the aperture (inlet) from the discharge chamber into the ionization chamber so that improved sensitivity will result. The relative size of the chambers, a smaller ionization chamber in particular, is also described as being important for detector sensitivity.

Although the design of discharge ionization detectors continues to be an object of study in the prior art, there nonetheless exists a need for a discharge ionization detector having a detector response that exhibits an improved dynamic range, lower minimum detectable level (MDL), and greater signal to noise ratio.

SUMMARY OF THE INVENTION

The present invention is directed to methods and apparatus for more efficient production and use of metastables and photons in a discharge ionization detector to thereby effect an improved dynamic range, lower minimum detectable level (MDL), and greater signal to noise ratio in the detector response.

Detector response in a discharge ionization detector is based on an accurate measurement of the ionized analyte of interest The efficiency of the generation of metastables and photons from a discharge in a volume of discharge gas will therefore establish certain advantageous characteristics of the detector response, such as the level of lowest measurable concentration of the analyte that can be detected.

The present invention is directed to the use of a discharge in a volume of discharge gas (preferable selected from a group of noble gases, and most preferably being helium or argon) that flows through a discharge chamber so as to cause metastables and photons to be generated in the discharge chamber. Such metastables and photons play an important role in the desired ionization of the electron-capturing species. However, we have found that conventional apparatus suffer from poor transfer of such metastables and photons to an ionization chamber. A loss of metastables via decay in the discharge chamber is predominant. We have further determined that conventional apparatus do not facilitate rapid flow of the discharge gas from the vicinity of the discharge in a discharge chamber to an ionization chamber, thus further inhibiting the delivery of metastables to the ionization chamber.

As a result of our findings, we have discovered an opportunity to achieve improved dynamic range, lower minimum detectable level (MDL), and greater signal to noise ratio in the detector response by facilitating greater transfer of metastables and photons to the ionization chamber in a discharge ionization detector.

One aspect of the present invention is thereby to provide a discharge ionization detector that employs a discharge chamber and means for effecting a discharge to provide ionization of an analyte in an adjacent ionization chamber, wherein the discharge source includes means for improved transfer of metastables and photons to the analyte present in the ionization chamber, thus to better effect ionization of the analyte.

In another aspect of the invention, ionization is particularly enhanced by provision of a flow guide located between the discharge chamber and the ionization chamber, wherein the flow guide directs a discharge gas fluid stream through the discharge and into the ionization chamber such that helium metastables are rapidly swept into the ionization chamber prior to the onset of decay. The abundance of metastables in the ionization chamber prior to such decay is then effective at improving the desired ionization of the analytes of interest.

In another aspect of the invention, ionization is particularly enhanced by provision of a flow guide which directs a discharge gas fluid stream through the discharge and into the ionization chamber such that photons are generated at a point from which the photons can more easily traverse the distance from the discharge to the ionization chamber, prior to the onset of decay. In particular, the flow guide is fashioned with an aperture array having bores situated with respect to the discharge so as to allow line of sight propagation of the photons from the discharge to the analyte. The abundance of photons in the ionization chamber prior to such decay is then effective at improving the desired ionization of the analytes of interest.

The flow guide also functions as an ion filter, wherein the flow of positively-charged discharge gas ions from the discharge chamber into the ionization chamber is suppressed The baseline current and the associated shot noise are thereby minimized.

In another aspect of the invention, a discharge ionization detector may be constructed wherein the detector response is characterized by improved measurement of analyte concentration, that is, a lower minimum detectable level of analyte concentration.

In another aspect of the invention, a discharge ionization detector may be constructed wherein the detector response is characterized by an increased dynamic range.

According to the preferred embodiments of the invention, there are provided a discharge source located in a discharge chamber, means for introducing discharge gas flow into the discharge chamber, a flow guide that directs discharge gas flow between the discharge chamber and an adjacent ionization chamber, means for introducing a flow of sample gas containing an analyte into the ionization chamber, and means for venting the sample gas and the discharge gas mixture from the ionization chamber. A plurality of apertures in the flow guide promote the flow of and metastables and the line of sight transfer of photons from the discharge at the- discharge source to the ionization chamber.

In a particular embodiment, the ionization chamber has an inlet port for receiving a sample gas as well as an outlet port for exhausting the sample gas and the discharge gas. A signal cathode is positioned in the ionization chamber and the wall of the ionization chamber is biased in a detector circuit with the signal cathode and an electrometer. Under appropriate conditions, the presence of analyte compounds in the ionization chamber alter the current flow from the signal electrode to the interior wall of the ionization chamber. The resulting change in current flow is a measure of the presence of constituent(s) in the analyte. The interior wall of the discharge chamber and the flow guide are biased in a discharge circuit and are configured so as to promote photon and metastable diffusion to the ionization chamber and also to block at least a substantial amount of the ionic current from passing to the signal cathode.

According to a preferred embodiment of the invention, a discharge ionization detector in accordance with the present invention may be constructed to include a detector body defining a first chamber in the form of a discharge chamber and a second chamber in the form of an ionization chamber, these first and second chambers being coaxially disposed and having a common internal wall shaped as a flow guide having an array of plural, closely-spaced parallel bores, wherein each bore includes input and outlet apertures therein. The body includes an inlet to the discharge chamber for admitting a discharge gas, preferably provided in the form of a pressurized stream of helium, and an inlet to the ionization chamber for admitting a flow of sample gas to be analyzed. The central region of the flow guide includes the array of plural bores so situated as to direct fluid flow in a direction from the discharge chamber to the ionization chamber, but to suppress fluid flow in the reverse direction. A discharge source includes an electrode assembly includes at least a discharge cathode situated an insulating sleeve- through the detector body so as to extend into the discharge chamber, and at least one protrusion situated in the interior wall of the discharge chamber, and preferably in the flow guide, at a location that is closely adjacent the input apertures. The protrusion extends into the volume of the discharge chamber and is opposite an exposed tip of the electrode assembly. The exposed tip on the discharge cathode is thus located proximate to the protrusion and to the plurality of bores. The discharge source is located so as to enable the creation of a discharge directly adjacent the region of the input apertures, and in particular is proximate at least some of the input apertures. The discharge created in the discharge source is thereby created in close proximity to the input apertures. In one preferred embodiment, the discharge cathode is coaxially mounted with respect to the input apertures and is biased in a high voltage circuit that includes the common wall, such that the tip of the discharge cathode and the protrusion cause a discharge to occur therebetween. The discharge is rapidly and effectively swept by the flow of the discharge gas into the input apertures and then to the ionization chamber. Metastables and photons generated in the discharge are thereby effectively swept into the ionization chamber for improved ionization of species in the column effluent.

A second electrode provided in the form of a signal cathode is mounted in an insulating sleeve in the detector body so as to project into the ionization chamber. A signal monitoring circuit may be constructed to include the signal cathode, a connection to the ionization chamber wall such that the ionization chamber wall acts as an electrode, means for biasing the signal cathode and the ionization chamber wall for generating an electric field with respect to the exposed portion of the signal cathode to cause positively-charged analyte ions to be accelerated toward the ionization chamber wall, and an electrometer for providing an indication of the analyte ionic current flow between the signal cathode and the ionization chamber wall so as to indicate the amount of ionized analyte components in the sample gas.

In one embodiment of the invention, the sample gas inlet to the ionization chamber preferably directs the flow of sample gas transversely to the flow of the discharge gas that enters the ionization chamber through the flow guide. The signal cathode is then centrally disposed within the ionization chamber and is located opposite the region of outlet apertures on the underside of the flow guide. In another embodiment of the invention, the sample gas inlet to the ionization chamber preferably directs the flow of sample gas in coaxial but opposite direction to the flow of the discharge gas that enters the ionization chamber through the flow guide. The signal cathode is then transversely disposed within the ionization chamber and is located laterally from the region of outlet apertures on the underside of the flow guide.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

FIG. 5A is a side perspective view.

DETAILED DESCRIPTION OF THE PREFERRED EMBODIMENTS

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of a novel discharge ionization detector for use in a gas sample analytical system. One particular application of the novel discharge ionization detector is in a chromatographic analytical system (hereinafter, a chromatography however, other applications such as process sampling systems, gas leak detection systems, air quality monitoring systems, and the like are contemplated.

Embodiments of the invention described herein are contemplated for use as a discharge ionization detector in a gas chromatograph. The preferred operation of the contemplated detector with respect to a conventional gas chromatograph may be understood as follows. In a chromatographic separation of a given sample compound, a sample is injected with a pressurized carrier gas into a separation column and the column effluent is directed as a fluid stream into the discharge ionization detector. One or more pneumatic manifold assemblies are envisioned, each of which serves in part to control and redirect a plurality of gas flows, including the carrier gas and a discharge gas. Accordingly, the pneumatic manifold may be operated to effect a modulation of any of the aforementioned gas flows, and in particular to supply modulated discharge gas flow to the discharge ionization detector described hereinbelow. Aspects of such gas supply in the embodiments illustrated in FIGS. 2 et seq. is preferably provided via electronic pneumatic control (EPC). For further details of electronic pneumatic control techniques, one may consult, for example, Klein, et al., U.S. Pat. No. 4,994,096 and U.S. Pat. No. 5,108,466, the disclosures of which are incorporated herein by reference.

Figure 1:
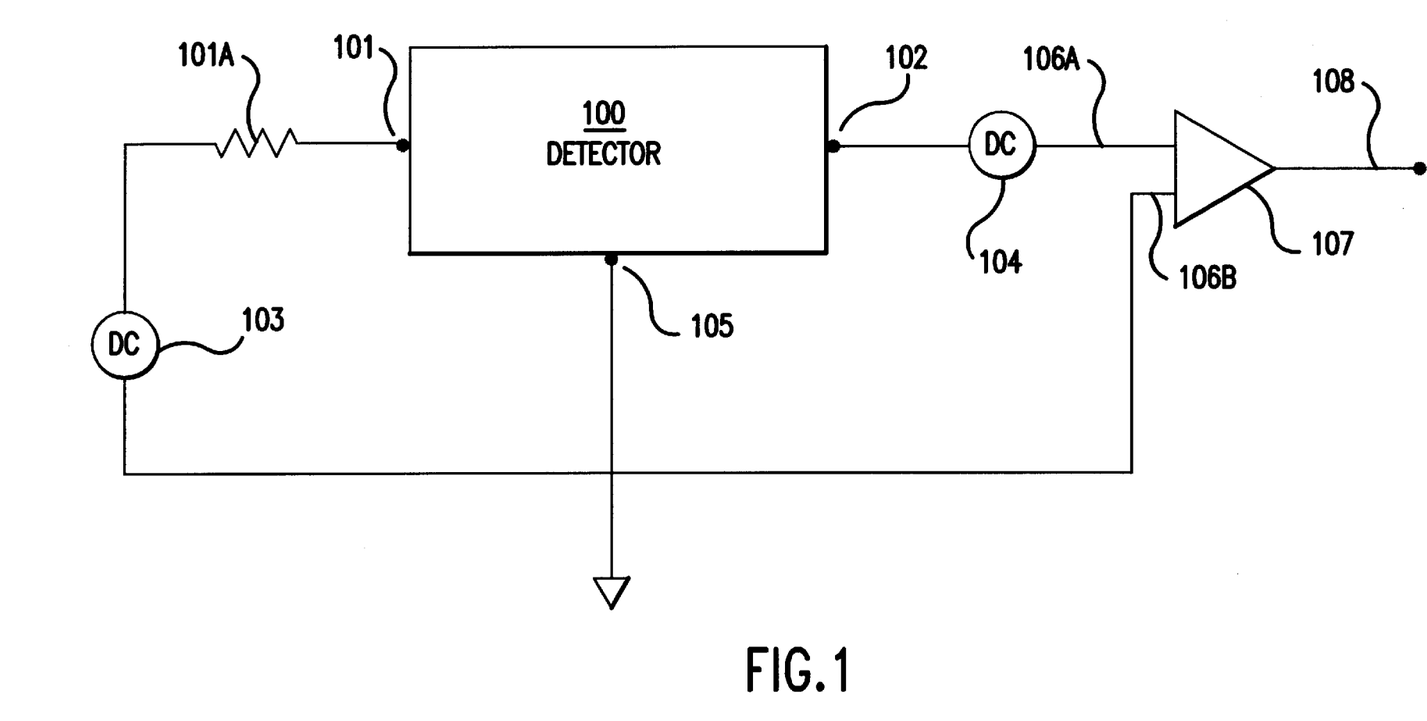
FIG. 1 is a simplified schematic view of a discharge ionization detector of the present invention.

As illustrated in FIG. 1, a preferred embodiment 100 of a discharge ionization detector constructed according to the invention includes a discharge cathode connector 101 connected in series to a resistor assembly 101A and a discharge voltage supply 103. The detector further includes a signal cathode connector 102, a signal bias voltage supply 104, and a common connector 105 (which is connected to a ground potential). Differential inputs 106A, 106B in an electrometer 107 may be connected to the signal bias voltage supply 104 and the common connector 105 so as to provide a detector output signal on a detector output signal line 108 for measuring the current passing between the signal cathode connector 102 and the common connector 105.

Figure 2:
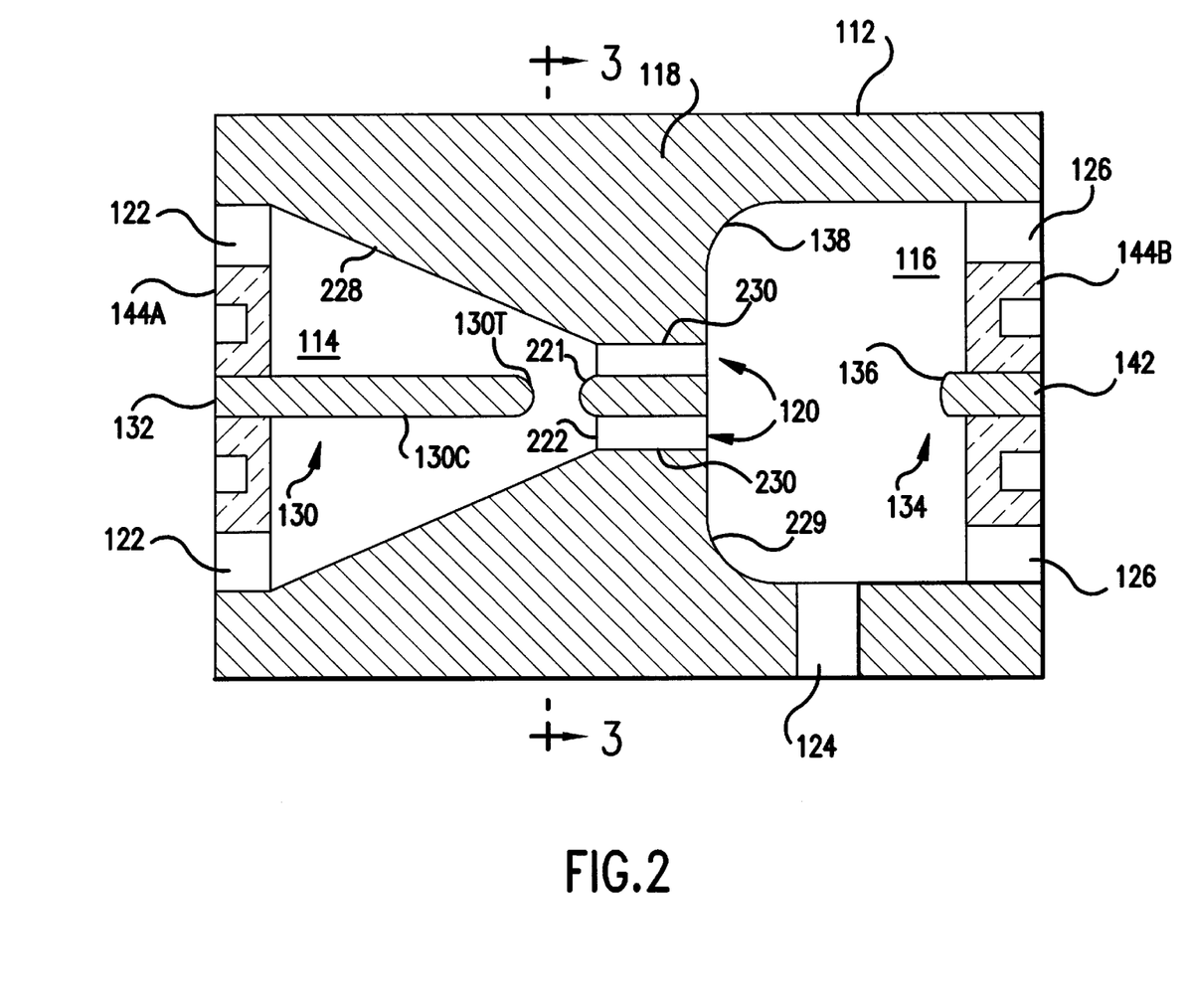
FIG. 2 is a schematic cross-sectional view of an embodiment of a portion of the discharge ionization detector of FIG. 1.
Figure 3:
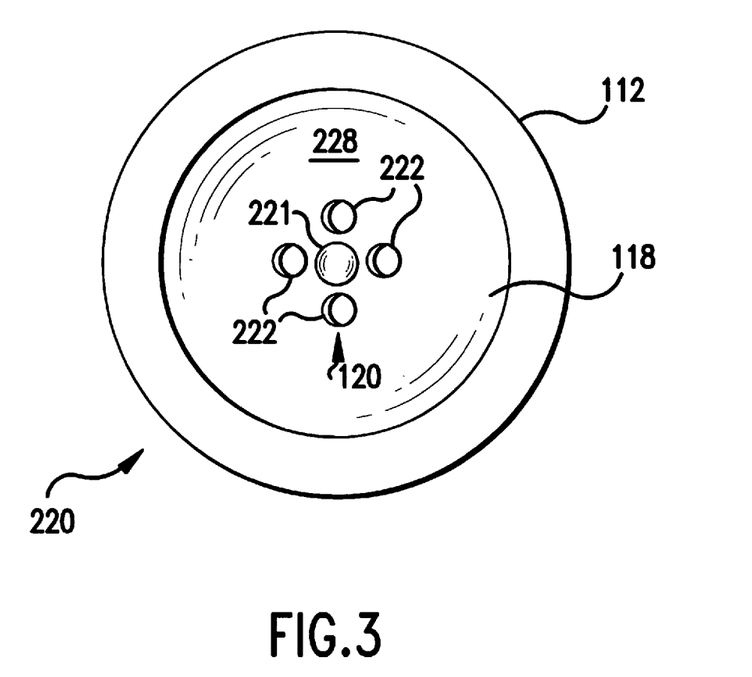
FIG. 3 is a sectional view of a flow guide in the detector shown in FIG. 2.

As illustrated in FIGS. 2–3, the preferred embodiment 100 of a discharge ionization detector constructed according to the invention includes a detector body 112 defining first and second chambers preferably constructed as discharge chamber 114 and ionization chamber 116, respectively, which are coaxially disposed and have a common internal wall 118 having an aperture array 120 therein. The volume of the ionization chamber 116 is preferably in the range of 25 to 250 microliters and in some applications may be less than one microliter and as large as 1 milliliter. The body includes inlets 122 for admitting a controlled flow of discharge gas, preferably one of the noble gases such as helium, and an inlet 124 to the ionization chamber 116 for admitting a sample gas having an analyte to be detected. In the illustrated embodiment, the sample gas input 124 directs the flow of sample gas transversely to the discharge of the discharge gas entering the chamber through the outlet ends of aperture array 120; however, other configurations are within the scope of the present invention. Vent outlets 126 in the ionization chamber 116 are also provided. A discharge source includes a first electrode assembly 130 provided in the discharge chamber 114. The first electrode assembly 130 includes a discharge cathode 130C for generating a discharge with respect to a portion of the common wall 118, such as a protrusion, that is situated adjacent the aperture array 120 such that desirable products of the discharge, such as metastables, are swept into the ionization chamber 116. In particular, the tip 130T of the first electrode assembly 130 is disposed in close proximity to, and in substantially coaxial alignment with, the center of the input apertures of the aperture array 120. The first electrode assembly 130 is connected, by way of an appropriate electrical connector 132, to a discharge voltage potential applied between the first electrode assembly 130 and the common wall 118.

A second electrode assembly 134 is provided in the ionization chamber 116. The second electrode assembly 134 includes a signal cathode 136, to be negatively charged, for generating an electric field with respect to the interior wall 138 of the ionization chamber 116. The signal cathode 136 preferable presents a small surface area to the ionization chamber 116 to avoid exposure to photons and the resulting noise artifacts. Preferably, the interior wall 138 and the common wall 118 are electrically coupled and thus are at the same potential voltage. The signal cathode 136 is provided with a negative charge by coupling through electrical connector 142 to a polarizing voltage source (supply 104 in FIG. 1). The interior wall 138 may be coupled to an electrometer by an appropriate electrical connector (connector 105 in FIG. 1), so as to provide for an indication of the amount of ionized components in the analyte.

In the illustrated embodiment, the signal cathode 136 is disposed within the ionization chamber 116 so as to be substantially coaxially aligned with the outlet ends of the aperture array 120. The tip 130T of the first electrode assembly 130 is disposed in close proximity to, and in substantially coaxial alignment with, the center of the input apertures of the aperture array 120. Hence, the detector body 112 is preferably constructed of a one or two-part cylindrical configuration. In the illustrated embodiment, the detector body 112 may be of a one-piece, unitary construction having the discharge and ionization chambers 114,116 machined therein. The discharge gas inlet 122, sample gas inlet 124, and vent outlets 126 may suitably be passageways extending through the sidewall of the detector body 112 into the respective chambers 114, 116. A major portion of the detector body 112 itself is electrically conductive and is preferably made of a metal material or other electrically conductive materials.

The electrode assemblies 130, 134 are respectively fitted in circular insulating adapters 144A, 144B that are each adapted to be placed into the detector body 112 to seal respectively the discharge chamber 114 and the ionization chamber 116. The adapters 144A, 144B are held in position by appropriate means (not shown). The discharge gas is conducted into the discharge chamber 114 via a suitable fitting (not shown) that may be mounted on the adapter 144A. The sample gas to be analyzed is conducted into the ionization chamber 116 via a suitable fitting mounted on the adapter 144B (not shown).

Referring to FIG. 3, an interior plan view of the common wall 118 is illustrated. The geometry of aperture array 120 is preferably such that the ratio of the length to the diameter of each of the bores 230 is greater than one, and is on the order of two to five. Such a geometry improves the line of sight traverse of photons from the discharge to the ionization chamber 116, and reduces back diffusion of analyte into the discharge chamber 114.

The common wall between the discharge chamber and the ionization chamber 116 is shaped as a flow guide 220 and is located at the common portion of the body 112 between the discharge chamber 114 and the ionization chamber 116. The flow guide 220 functions as a boundary to the active volume of the ionization chamber 116, the latter being defined as the region in which analyte ionization takes place. The flow guide 220 thereby separates the active volume from the discharge chamber 114. The flow guide 220 includes plural bores 230 that are preferably symmetrically arranged about a surface region in the flow guide that is proximate to the tip 130T; in particular, one or more protrusion(s) 221 may be provided. The arrangement of the bores 230 and a protrusion 221 facilitates the development of the desired discharge in the immediate vicinity of input apertures 222. For this purpose, the flow guide 220 and associated common connector 105 are electrically connected and similarly composed of a conductive material, such as stainless steel. The flow guide 220 is generally shaped like a disk, being thinner in the region of the bores 230, and having a generally cylindrical section with first and second major surfaces 228, 229 whereby the plurality of bores 230 extend through a central portion of the flow guide 220. Each bore 230 includes an input aperture 222 and an outlet aperture 224. Preferably the protrusion 221 is integral with the first major surface 228 so as to terminate in a bulbous region suitable for exciting the desired discharge. The flow guide 220 may alternatively be an insert fitted in the body 112 and sized such that its minor sides are engaged with the interior of the body when the flow guide 220 is fitted between the discharge chamber 114 and the ionization chamber 116.

The bores 230 facilitate the passage of discharge gas from the discharge gas inlet 122 and through the bores 230 into the ionization chamber 116 and thus towards the signal cathode 136. The discharge chamber 114 preferably exhibits a cup-shaped section being so designed and positioned such that the discharge gas can be rapidly swept through the glow discharge and into the input apertures 222 and then through the bores 230. The discharge chamber 114 preferably exhibits a cone-shaped section being so designed and positioned such that the sample gas can be directed as a pressurized stream into the ionization chamber 116. Further flow of the sample gas is constrained by the lower major surface 229 of the flow guide 222 and by the interior wall 138 of the ionization chamber 116 such that the mixture of the sample gas and the discharge gas is swept around the signal cathode 136. The mixture of the sample gas and the discharge gas is permitted to exit the ionization chamber 116 through the vents 126.

Another aspect of the illustrated embodiment is that the portion of the discharge gas that flows through the flow guide 220 is rapidly moved downstream from the glow discharge, due to the pressure of the discharge gas and the sufficiently small internal diameter of the bores 230. The rate of flow of the sample gas is slower in comparison to the flow rate of the discharge gas as it exits the outlet apertures 224 of the flow guide 220. The relatively slower rate of movement of the sample molecules in the ionization chamber 116, compared to the entry of the discharge gas into the ionization chamber 116, encourages a distribution and ionization of the sample molecules in the ionization chamber 116, while minimizing the migration of sample molecules into the discharge chamber 114.

Figure 4:
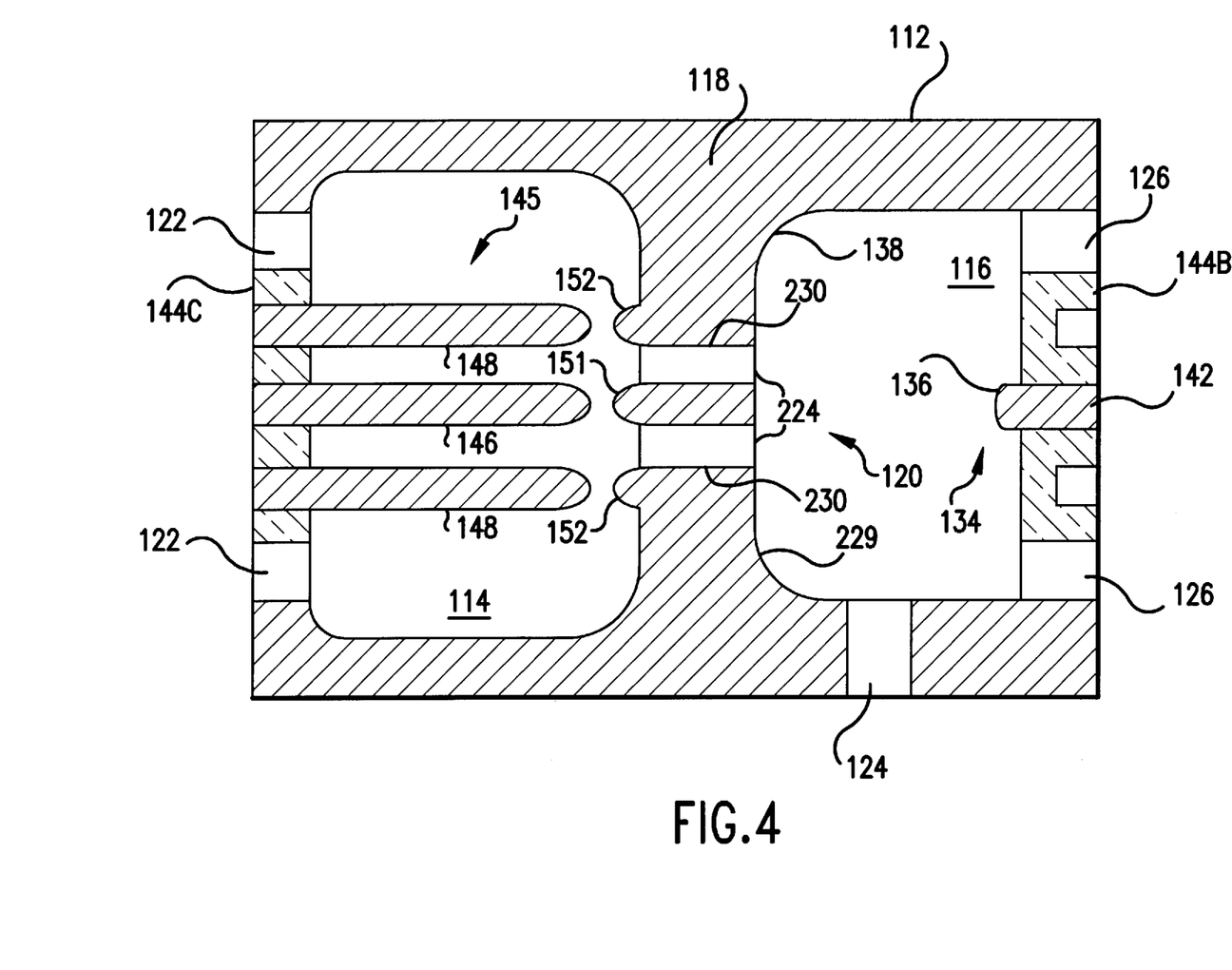
FIG. 4 is a schematic cross-sectional view of an alternative embodiment of the portion of the discharge ionization detector of FIG. 1.
Figure 5A:
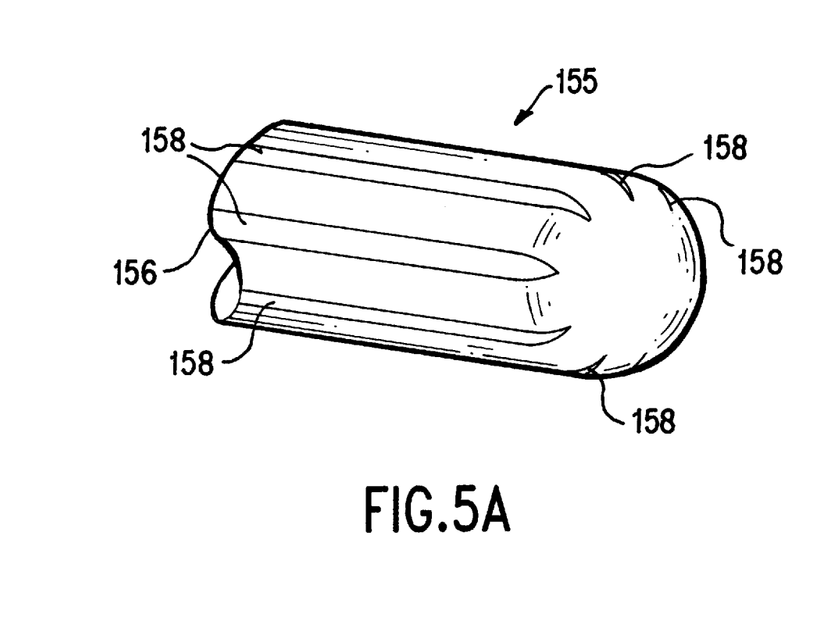
Figure 5B:
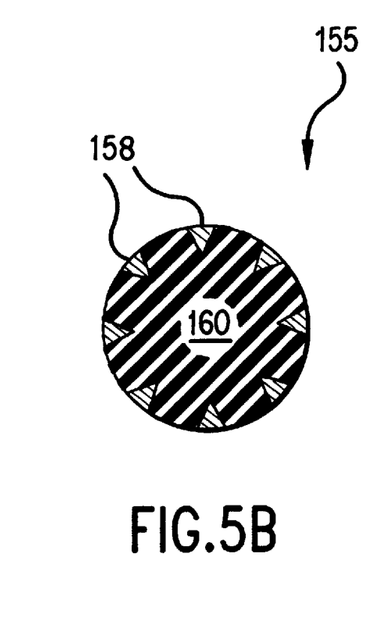
FIG. 5B is a sectional view, respectively, of an alternative embodiment of an electrode for use in a first electrode assembly in the detector shown in FIG. 2.

As illustrated in FIG. 2, a preferred embodiment of the discharge electrode assembly 130 may be constructed to include a single electrode element 130C. As illustrated in FIGS. 4 and 5, alternative embodiments of the discharge electrode assembly 130 are contemplated. One such alternative embodiment 145 may be constructed to include at least one inner element 146 and at least one outer element 148 disposed within an appropriately-configured adapter 144 so as to oppose respective protrusions 151, 152. Another alternative embodiment 155 may be constructed to include at least one inner element 156 having a plurality of conductive sections 158 embedded in an electrically-insulating core 160 that may be separately biased so as to cause an array of respective individual discharges with respect to respectively proximate portions of the major surface 228.

What is claimed is:

1. A discharge ionization detector for detection of an analyte, comprising:
   a discharge chamber;
   an ionization chamber located adjacent to the discharge chamber;
   means for providing the analyte in the ionization chamber;
   discharge means including an inlet for admitting a stream of discharge gas into the discharge chamber for effecting a discharge to provide a plurality of metastables in the discharge chamber;
   wherein the discharge chamber and the ionization chamber include a common internal wall having an aperture therein for causing the stream of discharge gas to pass through the discharge and subsequently through the aperture, thereby effecting rapid transfer of the metastables from the discharge to the analyte present in the ionization chamber, whereby ionization of the analyte is enhanced.

2. The detector of claim 1, wherein the common internal wall further comprises:
   a flow guide located between the discharge chamber and the ionization chamber, wherein the flow guide includes said aperture in an aperture array for directing the discharge gas fluid stream through the aperture array and into the ionization chamber, wherein metastables are rapidly swept into the ionization chamber prior to the onset of decay.

3. The detector of claim 1, wherein the aperture is constructed for permitting line of sight transfer of photons from the location of the discharge to the location of the analyte in the ionization chamber prior to the onset of decay.

4. The detector of claim 3, wherein the aperture is provided in the form of an aperture array having a plurality of bores coaxially situated with respect to the discharge and the ionization chamber so as to allow line of sight propagation of the photons from the discharge chamber to the location of the analyte.

5. The detector of claim 2, wherein the discharge chamber includes a discharge cathode located proximate to the aperture array, wherein the aperture is situated with respect to the discharge cathode so as to direct discharge gas fluid stream from the vicinity of the discharge and through the aperture to the ionization chamber.

6. A discharge ionization detector for detection of an analyte, comprising:
   a discharge chamber;
   an ionization chamber located adjacent to the discharge chamber;
   discharge means located with respect to the ionization chamber for effecting a discharge to provide a plurality of metastables;
   means for introducing discharge gas flow into the discharge chamber;
   means for introducing a flow of sample gas containing an analyte into the ionization chamber,
   means for venting the sample gas and the discharge gas mixture from the ionization chamber; and
   a flow guide situated between the discharge chamber and the ionization chamber for directing discharge gas flow from the discharge chamber to the ionization chamber, the flow guide having an aperture to cause the discharge gas flow to sweep the discharge and thereby direct a plurality of metastables to the ionization chamber, and to provide a line of sight transfer of photons from the vicinity of the metastable generated in the discharge chamber to the ionization chamber.

7. The detector of claim 6, wherein the discharge means includes a discharge electrode assembly having a central electrode surrounded by a plurality of spaced additional electrodes, each of the central electrode and the additional electrodes having an exposed tip, and further comprising a respective plurality of protrusions in the flow guide each respectively situated adjacent a selected one of the exposed tips of the central electrode and the additional electrodes.

8. The detector of claim 6, wherein the discharge means includes a discharge electrode assembly having a central electrode having integrated therein a plurality of spaced conductive sections, each of the sections having an exposed tip, and further comprising a respective plurality of protrusions in the flow guide each respectively situated adjacent a selected one of the exposed tips of the central electrode.

9. A discharge ionization detector for detection of an analyte, comprising:

a detector body defining a first chamber in the form of a discharge chamber and a second chamber in the form of an ionization chamber, the first and second chambers being coaxially disposed and having a common internal wall shaped as a flow guide having an array of plural, closely-spaced parallel bores, wherein each bore includes input and outlet apertures therein wherein a central region of the flow guide includes an array of plural bores so situated as to direct fluid flow in a direction from the discharge chamber to the ionization chamber, but to suppress fluid flow in the reverse direction;

an inlet in the discharge chamber for admitting a discharge gas provided in the form of a pressurized stream;

an inlet in the ionization chamber for admitting a flow of sample gas to be analyzed; and a discharge source including an electrode assembly having at least a discharge cathode situated an insulating sleeve through the detector body so as to extend into the discharge chamber, and at least one protrusion situated in at least one of the interior wall of the discharge chamber and the flow guide, the protrusion being located closely adjacent the input apertures and extending into the volume of the discharge chamber so as to be an exposed tip of the electrode assembly;

wherein the exposed tip on the discharge cathode is located proximate to the protrusion and to the plurality of bores and the discharge source is located so as to enable the creation of a discharge directly adjacent at least some of the input apertures.

10. The detector of claim 9, further comprising:

a signal cathode located in the ionization chamber, and means connected to the body, discharge cathode, and signal cathode for biasing the signal cathode and the discharge cathode, wherein the discharge cathode and the signal cathode are biased negatively with respect to the body.

* * * * *